United States Patent [19]

Fukui et al.

[11] 4,174,407
[45] Nov. 13, 1979

[54] ANTIVIRAL AGENT

[75] Inventors: Masaru Fukui, Takarazuka; Shigeo Ogino, Nishinomiya; Hisao Yamamoto, Kobe, all of Japan

[73] Assignees: Sumitomo Chemical Company, Limited, Osaka; Kao Soap Co., Ltd., Tokyo, both of Japan

[21] Appl. No.: 869,144

[22] Filed: Jan. 13, 1978

[51] Int. Cl.$^2$ ............................................. A61K 31/13
[52] U.S. Cl. ..................................................... 424/325
[58] Field of Search ........................................ 424/325

[56] References Cited
U.S. PATENT DOCUMENTS 3,397,233  8/1968  Cairns .................................. 424/325

OTHER PUBLICATIONS

Aigami et al., J. Med. Chem., 1976, vol. 19, No. 4, pp. 536–540.

Primary Examiner—Jerome D. Goldberg
Attorney, Agent, or Firm—Stevens, Davis, Miller & Mosher

[57] ABSTRACT

Viral infections caused by viruses belonging to Herpes and Influenza groups can be controlled by administering an effective amount of 3-amino-4-homoisotwistane of the formula,

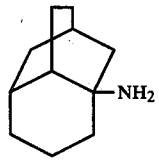

1 Claim, 1 Drawing Figure

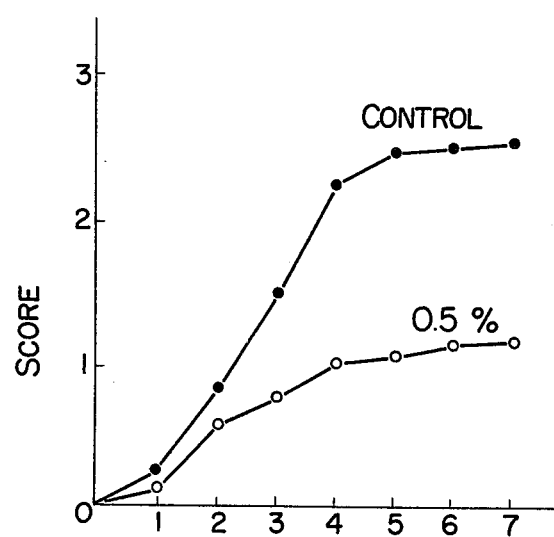

ANTIVIRAL AGENT

This invention relates to an antiviral agent which comprises 3-amino-4-homoisotwistane or its salt as an active ingredient and a pharmaceutically acceptable carrier.

3-Amino-4-homoisotwistane hydrochloride (hereinafter referred to as compound A) was reported by Aigami et al. to show antiviral effects on Newcastle disease virus (J. Med. Chem. 19, 536, 1976), but has never been so far reported to show the other antiviral activities.

The present inventors have studied in detail the antiviral activities of the coumpound A, and proved that the compound possesses the very strong antiviral activities on herpes and influenza viruses.

The compound A can be synthesized, for example, according to the methods described in "The Journal of Medicinal Chemistry", Vol. 19, p. 536 (1976).

It is well known that the so-called "caged compounds" such as amantadine often show the anti RNA viral activites but rarely exhibit the anti DNA viral activities. Among the caged compounds, only tromantadine is known to show an anti DNA viral activities. The antiviral effects of the compound A on herpes virus and so on are much superior to those of tromantadine. Thus, it can be said that the compound A is a very effective antiviral agent.

In the following, the antiviral activities, effective dosages, toxicities of the compound A are described.

Ex. 1. Effects of the compound A on the growth of herpes virus in tissue cultures Antiviral activities were determined by tube dilution method. The used cells for the assay were HeLa cells and KB cells. HeLa cells were cultured in YLE medium and KB cells were cultured in Eagle MEM medium. Medium was supplemented with 10% fetal calf serum. The monolayer of cells grown in tube was exchanged to the fresh medium supplemented with 2% fetal calf serum, then 1000 $TCD_{50}$ of herpes simplex type 1 (HF strain) and the test compound were added.

After 72 hr. incubation at 37° C. virus induced cytopathic effect (CPE) and the cytotoxicity of the compound were determined by microscopic examination. Minimum virus growth inhibition concentration (MIC) and minimum cytotoxic concentration (MCC) were shown in Table. I.

Table I.

The effect of the compound A on growth of Herpes simplex virus

| Drugs | Host cells | MIC ($\mu$g/ml) | MCC ($\mu$g/ml) |
|---|---|---|---|
| Compound A | HeLa | 5 | 50 |
|  | KB | 5 | 50 |
| Amantadine HCl | HeLa | 50 | >50 |
|  | KB | 50 | >50 |
| Tromantadine | KB | 25 | >50 |

Ex. 2. Therapeutic effects of the compound A on experimental herpes virus infection Therapeutic effects were determined by using two experimental infections as follows.

(i) Effects on herpeskeratitis

The corneal epithelium of each eye of rabbit was anesthetized and scratched, then each eye was infected with herpes simplex virus type 1 (HF strain). One of each infected eyes was used for treatment with the compound A and the other was used for viral control. One half % eye lotion of the compound A in 1.4% polyvinyl alcohol was applied every two hours, five times a day during 7 days 12 hr. after virus infection. Each eye was daily examined and scored the lesion on the conjunctiva, cornea and the iris for 7 days. In this score 0 means normal and 4 means maximal severity. The eyes scratched but not infected with virus were similarly treated with compound A in parallel as toxicity control. The results were shown in FIG. 1.

In FIG. 1, the numbers on the axis of abscissa indicate the day after the viral infection and those on the axis of ordinate indicate the score [0(normal)- 4(maximal severity)], and the mark —o— indicates the score of an eye lotion which contains 0.5% compound A and the mark —●— indicates that of control.

One half percent eye lotion of the compound A did not prolong the cure period as compared with control, nor showed any other toxicities.

(ii) Effects on herpesencephalitis

Mice were anesthetized with ether and were infected intracerabrally (i.c.) with 30 $LD_{50}$ of herpes simplex virus type 1 HF strain. Infected mice were treated with various therapeutic schedules. The antiviral effects of the compound A was determined by comparing the number of survivors at 3 weeks after viral infection and the mean survival days of the drug-treated and placebo-treated animals. The results were shown in Table 2.

Table II.

| Dose[a] (mg/kg) | Administration[b] route | Mean[c] survival days | Survival[d] ratio (no. of survivors/ no. of total mice) |
|---|---|---|---|
| 5 |  | 7.2 | 7/10 |
| 0 | i.c. | 5.6 | 0/10 |
| 100 |  | 7.8 | 3/10 |
| 0 | p.o. | 5.9 | 0/10 |
| 100 |  | 7.6 | 5/10 |
| 0 | s.c. | 5.8 | 0/10 |
| 10 |  | 8.0 | 2/10 |
| 0 | i.v. | 6.2 | 0/10 |

The effects of the compound A on herpesencephalitis.

(a) Dose of administration
(b) Schedule of administration of each route was as follows,
 i.c. (intracerebrally): single administration simultaneously with virus infection
 p.o (per os): twice administration per day during 8.5 days from 4 hr. after virus infection
 s.c. (subcutaneously): twice administration per day during 8.5 days from 4 hr. after virus infection
 i.v. (intravenously): single administration at 3 hr. after virus infection
(c) The animals were examined for 21 days and deaths occuring were recorded.
(d) Survivors at 21st day.

Ex. 3. Acute toxicity of the compound A

Acute toxicities of the compound A against mice were compared with Amantadine (Symmetrel®). The results were described in Table III.

Table III.

Acute toxicities of the compound A against mice

| Drugs | LD$_{50}$ (mg/kg) p.o. | LD$_{50}$ (mg/kg) i.v. |
|---|---|---|
| Compound A | 300 | 32 |
| Amantadine | 400 | 49 |

Ex. 4. Effects of the compound A on experimental Influenza virus infection

The antiviral activities were determined by the modified Horsfall's method (Tani et al., Fukuoka Igaku Zasshi, 58, 9 (1967)).

Drug preparation

The compound A and amantadine hydrochloride as a control were dissolved in sterile physiological saline for injection.

Animals ddY male mice weighing about 12 g were used in this study. Ten animals were used at each experiment.

Virus

Influenza A$_o$PR/8 was used.

Drug evaluation

Five LD$_{50}$ of influenza A$_o$PR/8 was used for infecting mice by the aerosol. Subcutaneous drug treatment using various dosages started at 3 hours pre, 2, 6, 18, 30, 42, 54, 66, 78, 90, 102, 114, 126, 138 and 150 hours post infection in order to determine the efficacy of the compound A and amantadine hydrochloride.

Lung lesion score (LLS) was determined 7 days after infection by sacrificing the animals. When the mice were died within 7 days after infection, LLS determination was also carried out.

Results were as follows;

| Exp. No. | Drug | dose (mg/kg) | Lung Lesion Score |
|---|---|---|---|
| 1 | 0 | | 4.8 |
| 2 | amantadine HCl | (10 mg/kg) | 4.3* |
| 3 | " | (25 mg/kg) | 4.1* |
| 4 | " | (50 mg/kg) | 4.0* |
| 5 | compd. A | (7.5 mg/kg) | 4.6 |
| 6 | " | (15 mg/kg) | 4.0* |
| 7 | " | (30 mg/kg) | 4.2* |

*$P<0.05$ (Probability value, Student's t test)

As mentioned above, the compound A shows a very strong antiviral activities in vivo as well as in vitro, and can be used for the therapy of human herpes viral diseases, for example, herpes keratitis, herpesencephalitis and herpeslabialis, and human influenza infections in the pharmaceutical forms such as an ointment, eye lotion, injection, tablet and so on.

The dose of the compound A used in the treatment for an adult is varied by administration routes. When used in a formula of ointment or eye lotion, the dosage level of 0.1–0.5% concentration, preferably 0.2%, which is administered several times per day, is desirable.

When administered orally or subcutaneously, 100–500 mg, preferably some 200 mg per day is desirable, and when administered intraveneously, 10–50 mg, preferably 10 mg per day is desirable.

The said compound A can be formulated to ointment, eye lotion, injection, tablet, capsule, troche and so on in a manner well-known to pharmaceutical chemists reffering to the representative antiviral agents.

In the following, the pharmaceutical uses of the present invention are described.

Example 1.

Eye lotion

| | |
|---|---|
| β-Phenylethylalcohol | 5 ml |
| 3-Amino-4-homoisotwistane HCl | 5 g |
| Saline water | 995 ml |
| Total volume | 1000 ml |

The materials were dealt aseptically.

EXAMPLE 2.

Ointment

One half percent of 3-amino-4-homoisotwistane HCl in liquid paraffin. The materials were dealt aseptically.

EXAMPLE 3.

Tablet

| | |
|---|---|
| 3-Amino-4-homoisotwistane HCl | 100 mg |
| Sucrose | 88 mg |
| Kaolin | 150 mg |
| Potato starch | 20 mg |
| Magnesium stearate | 5 mg |

Tablets were prepared according to usual pharmaceutical methods. Easily soluble film coating tablets are, if necessary, able to be prepared by usual methods.

EXAMPLE 4.

Injection

Sterile 3-amino-4-homoisotwistane HCl (10 mg) was aseptically put into an ampoule and sealed to prevent from humidity and microbiral contamination. Before use, it can be dissolved into 2 ml of 5% injectable glucose solution. It can be also used by dissolving with 2 ml of 0.9% injectable saline.

What is claimed is:

1. A method for the treatment of viral infectious diseases caused by herpes or influenza viruses which comprises administering an amount pharmaceutically effective for the treatment of said infectious diseases of 3-amino-4-homoisotwistane of the formula,

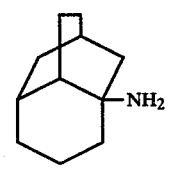

to a patient suffering from said infectious diseases.

* * * * *